United States Patent [19]
Heinecke

[11] Patent Number: 6,133,039
[45] Date of Patent: *Oct. 17, 2000

[54] IN VIVO METHOD FOR DETERMINATION OF OXIDATIVE STRESS

[75] Inventor: Jay W. Heinecke, St. Louis, Mo.

[73] Assignee: Washinton University, St. Louis, Mo.

[*] Notice: This patent is subject to a terminal disclaimer.

[21] Appl. No.: 09/484,884

[22] Filed: Jan. 18, 2000

Related U.S. Application Data

[63] Continuation-in-part of application No. 09/170,513, Oct. 13, 1998.
[60] Provisional application No. 60/074,167, Feb. 9, 1998.
[51] Int. Cl.[7] .................................................. G01N 33/00
[52] U.S. Cl. ............................. 436/89; 436/86; 436/811
[58] Field of Search ............................... 436/86, 89, 811

[56] References Cited

U.S. PATENT DOCUMENTS 5,731,208  3/1998  Heinecke .

OTHER PUBLICATIONS

Berliner & Heinecke: Free Radical Biol. & Medicine, vol. 20, pp. 707–727 (1996).
Heinecke; Cur. Opinions Lipid, vol. 8, pp. 268–274 (1997).
Heinecke et al; J. Biol. Chem., vol 268, pp. 4069–4077 (1993).
Leeuwenburgh et al; J. Biol. Chem. vol. 272, pp. 3520–3526 (1997).
Heinecke et al; J. Clin. Invest., vol. 91, pp. 2866–2872 (1993).
Leeuwenburgh et al; Am. J. Physiol., vol. 274, pp. R453–R461 (1998).
Leeuwenburgh et al; Free Radical Biol. & Medicine, vol. 27, pp. 186–192 (1999).
Jacob et al; J. Biol. Chem., vol. 271, pp. 19950–19956 (1995).
McCormick et al; J. Biol. Chem., vol. 273, pp. 32030–32037 (1998).
Leeuwenburgh et al; Arch. Biochem. Biophys., vol. 346, pp. 74–80 (1997).
Leeuwenburgh et al; J. Biol. Chem., vol. 272, pp. 1433–1436 (1997).
Hazen & Heinecke; J. Clin. Invest., vol. 99, pp. 2075–2081 (1997).
Hazen et al.; J. Biol. Chem., vol. 271, pp. 1861–1867 (1996).
Heinecke; FASEB J., Col. 13, pp. 1113–1120 (1999).

*Primary Examiner*—Jill Warden
*Assistant Examiner*—Monique T. Cole
*Attorney, Agent, or Firm*—Scott J. Meyer

[57] ABSTRACT

A non-invasive method for the determination of oxidative stress in a patient by urinalysis is disclosed. The method comprises quantifying the level of o,o'-dityrosine in a sample of the urine of said patient and comparing with the corresponding level of said compound in a normal or control sample, whereby a substantially elevated level of said o,o'-dityrosine is indicative of oxidative stress in said patient.

2 Claims, 9 Drawing Sheets

IN VIVO METHOD FOR DETERMINATION OF OXIDATIVE STRESS

This is a Continuation-in-Part of application Ser. No. 09/170,513, filed Oct. 13, 1998, which is a Continuation-in-Part of application Ser. No. 60/074,167, filed Feb. 9, 1998.

This invention was made in part with government support under grant number A12293 awarded by the National Institutes of Health. The government has certain rights in the invention.

FIELD OF THE INVENTION

The present invention relates to a non-invasive method for the determination of oxidative stress in a patient by urinalysis.

BACKGROUND OF THE INVENTION

[Note: Literature references for the following background information and on conventional test methods and laboratory procedures well known to the ordinary person skilled in the art, and other such state-of-the-art techniques as used herein, are indicated by reference numbers in parenthesis and appended at the end of the specification.]

Oxidative modification of biomolecules may contribute to the pathogenesis of disorders ranging from atherosclerosis to diabetes to ischemia-reperfusion injury (1–3). It also may play a role in the aging process itself (4,5). Important targets for oxidation include proteins, which play fundamental roles as biological catalysts, gene regulators, and structural components of cells (6–9). A well-characterized pathway for generating oxidants involves the NADPH oxidase of phagocytes. This membrane-associated electron transport chain produces superoxide ($O_2^{\cdot -}$) (10).

$$NADPH + O_2 \rightarrow NADP^+ + O_2^{\cdot -}$$

The superoxide then dismutates to form hydrogen peroxide ($H_2O_2$), which serves as an oxidizing substrate for myeloperoxidase, a heme protein secreted by activated phagocytes (6–9).

The NADPH oxidase system plays a key role in host defenses against microbial pathogens, and its importance is illustrated by clinical features of chronic granulomatous disease (CGD). In this genetic disorder, defects in components of the oxidase impair $O_2^{\cdot -}$ production, rendering patients vulnerable to recurrent bacterial and fungal infections (6–9,11,12). Mice made deficient in NADPH oxidase simulate the CGD phenotype (13).

Although oxidants generated by phagocytes are critical to host defenses, they may also damage tissue at sites of inflammation (1,14). It has been difficult to evaluate their pathogenic roles, however, because many of the current methods are nonspecific and prone to artifacts. In contrast, analyzing normal and diseased tissue for specific markers has proved to be a powerful approach to studying oxidative damage in vivo (15). Such markers have been identified in vitro by searching for stable products of protein oxidation. For example, oxidatively damaged proteins may contain o,o'-dityrosine cross-links, which can be generated through a variety of mechanisms. These may involve peroxynitrite, nitrogen dioxide radical, hydroxyl radical, or the myeloperoxidase-peroxide system of activated phagocytes, which cross-links tyrosine residues (16–19). Tissue levels of o,o'-dityrosine are elevated in atherosclerosis, exercise, Alzheimer's disease, and aging (20–23). Oxidative stress has been linked to all of these conditions.

Dityrosine also may mark oxidatively damaged proteins for proteolytic destruction because red blood cells exposed to $H_2O_2$ release this abnormal amino acid, suggesting that its formation in proteins may lead to protein breakdown (24).

The present inventor has proposed that oxidized amino acids might be excreted from cells rather than being re-used for protein synthesis. After entering the blood, they would be filtered by the kidney into urine. The demonstrations in the priority applications, Ser. No. 60/074,167 and 09/170,513, that levels of urinary o,o'-dityrosine are elevated in exercised and aging animals and that antioxidant therapy decreases these levels, is consistent with this proposal (21, 22).

BRIEF DESCRIPTION OF THE INVENTION

In accordance with the present invention, a non-invasive method for the determination of oxidative stress in a patient by urinalysis is provided. The method comprises quantifying the level of o,o'-dityrosine in a sample of the patient's urine and comparing with the corresponding level in a normal or control sample. A substantially elevated level of that amino acid is indicative of oxidative stress in the patient.

The finding of a substantially elevated level of o,o'-dityrosine in the urine of a patient subject to oxidative stress was unexpected since amino acids are normally broken down or resorbed during the usual metabolic processes in the body for several reasons:

First, amino acids are generally known to be almost completely resorbed from glomular filtrate in the proximal tubule of the kidney. See, for example, TEXTBOOK OF MEDICAL PHYSIOLOGY, by Arthur C. Guyton, M.D., Eighth Edition, 1991, W. B. Saunders Company, pp. 303–304.

Secondly, the oxidized amino acid, o,o'-dityrosine, is shown herein to be excreted from the blood into urine almost quantitatively. This is a critical finding in accordance with the present invention for providing a non-invasive method for the determination of oxidative stress in a patient. If, instead, only a minor fraction of the amino acid were excreted into urine, changes in the excretion rate (or metabolism rate; see below) rather than oxidative stress might account for changes in urine level.

The observation that dityrosine is excreted nearly quantitatively was unexpected for several reasons. First, as noted above, it is surprising that dityrosine itself is excreted in vivo in urine at all. Second, this indicates that dityrosine injected intravenously is not metabolized to other compounds. Most amino acids transfer their amino groups (which are an important cellular nutrient) to acceptor molecules when they are degraded. See, for example, TEXTBOOK OF MEDICAL PHYSIOLOGY, id, at page 768.

A striking example of the typical metabolic fate of amino acids is observed with the oxidized amino acid 3-nitrotyrosine. Minimal amounts of this amino acid (a marker of reactive nitrogen species) are excreted into urine when 3-nitrotyrosine is given to animals. See, for example, Tabrizi-Fard, et al., Drug Metab. Dispos. 27(4), 429–431 (1999). Instead, metabolites of the amino acid such as 3-nitro-4-hydroxyphenylacetic acid, 3-nitro-4-hydroxyphenyllic acid, and possibly other species appear in urine. Tabrizi-Fard, id, and Ohshimi et al., Food Chem. Toxicol. 28(9), 647–652 (1990).

Collectively, these findings indicate that it is not obvious that dityrosine would be quantitatively excreted in urine, and they support the inventor's contention that quantifying the level of o,o'-dityrosine in urine is a useful, non-invasive and unobvious method to assess oxidative stress in a patient.

DETAILED DESCRIPTION OP THE INVENTION

While the specification concludes with claims particularly pointing out and distinctly claiming the subject matter regarded as forming the present invention, it is believed that the invention will be better understood from the following preferred embodiments taken in conjunction with the accompanying drawings.

BRIEF DESCRIPTION OF THE DRAWINGS

FIG. 1 is a graphical representation, shown in two parts FIGS. 1A and 1B, in which urinary levels of Dityrosine/Creatinine, nmol/mol, are plotted against time in hours.

FIG. 1 thus shows urinary levels of o,o'-dityrosine in wild-type (FIG. 1A) and CGD mice (FIG. 1B). Animals were injected with saline (Control), thioglycollate (Thio) and zymosan as described in Examples hereinbelow. Urine was collected at the indicated times and subjected to solid-phase extraction on a C-18 column. Isolated amino acids were derivatized and subjected to isotope dilution negative ion electron capture GC/MS analysis with selected ion monitoring. Results represent the mean of three animals. *$p<0.0005$ compared with control, Student's t test.

FIG. 2 is graphical representation, shown in two parts FIGS. 2A and 2B, in which tissue levels of Dityrosine/Tyrosine, mmol/mol, are plotted against time in hours in FIG. 2A and after 3 hours in FIG. 2B.

FIG. 2. thus shows tissue levels of o,o'-dityrosine in wild-type (FIGS. 2A and 2B) and CGD mice (FIG. 2B). Thioglycolate-elicited peritoneal inflammatory cells were activated in vivo with zymosan. FIG. 2A: At the indicated time (n=3 animals) or FIG. 2B: 3 h after injection of zymosan, protein-bound o,o'-dityrosine in cellular proteins was quantified by isotope dilution GC/MS.

FIG. 3 is graphical representation, shown in two parts FIGS. 3A and 3B, in which Dityrosine, Counts/$\mu$l are plotted against time in minutes in FIG. 3A, and in which the % of Injected Dityrosine recovered after one, three and 4 hours is plotted for various tissues and urine in FIG. 3B. The tissues are blood, heart, spleen, liver and kidney.

FIG. 3 thus shows metabolic fate of radiolabeled o,o'-dityrosine injected intravenously into mice. Mice were injected with 2×10$^5$ cpm of [$^{14}$C]dityrosine. FIG. 3A: Blood was collected at the indicated times by retroorbital bleeding.

FIG. 4 thus shows HPLC analysis of urine of animals injected intravenously with radiolabeled o,o'-dityrosine. Urine collected from animals injected with [$^{14}$C]dityrosine was subjected to reverse-phase HPLC analysis with monitoring of radioactivity by scintillation spectroscopy.

FIG. 5 is graphical representation of Mass Spectrometry, shown in two parts FIGS. 5A and 5B, in which Ion Current is plotted against time in minutes in FIG. 5A, and in which levels of Dityrosine/Creatinine, nmol/mol, are plotted for urine in healthy (Control) and Septic humans in FIG. 5B.

FIG. 5 thus shows mass spectrometric detection of o,o'-dityrosine in human urine. FIG. 5A: Human urine was subjected to solid-phase extraction. The n-propyl ester, per heptafluorobutyryl derivatives of the reisolated amino acids were subjected to negative ion electron capture GC/MS with selected ion monitoring. Note co-elution of ion expected for o,o'-dityrosine (m/z 1030 (M-HFB)$^-$ and 1208 (M-HF)$^-$) with those of $^{13}$C$_{12}$ labeled internal standard (m/z 1042 and 1220).

In order to illustrate the invention in greater detail, the following specific laboratory examples were carried out. Although specific examples are thus illustrated herein, it will be appreciated that the invention is not limited to these specific examples or the details therein.

In these Examples, it was first determined whether phagocyte activation promotes oxidative tissue damage by determining levels of o,o'-dityrosine in inflammatory cells isolated from the peritoneum of wild-type and CGD mice. Isotope dilution gas chromatography/mass spectrometry (GC/MS), a sensitive and specific method, was used in these Examples. Levels of o,o'-dityrosine rose transiently in the proteins of the leukocytes of the wild-type animals, as did the amount of o,o'-dityrosine excreted in urine. These increases failed to occur in the CGD mice, indicating that protein oxidation under these in vivo conditions requires the participation of the NADPH oxidase of activated phagocytes. These results indicate that oxidized tissue proteins undergo proteolysis and that the resulting free o,o'-dityrosine is excreted in urine (4,24–26). They strongly support the present contention that oxidized amino acids in urine represent a noninvasive marker of oxidative stress in vivo. Moreover, a striking increase in urinary o,o'-dityrosine was detected in patients with systemic inflammation. Clinical tests based on such a marker would be invaluable for the assessment of oxidative stress in human disease.

EXAMPLES

Materials.

Unless otherwise indicated, reagents were obtained from Sigma Chemical Company (St. Louis, Mo.) or Aldrich Chemical (Milwaukee, Wis.). Organic solvents were HPLC grade.

Animal Studies.

The animal studies committee of Washington University School of Medicine in St. Louis approved all protocols. The C57BL/6J mice used for these experiments were obtained from Jackson Laboratories (Bar Harbor, Mass.) and bred and maintained under pathogen-free conditions. Impaired $O_2^{\bullet-}$ by phorbol ester-stimulated neutrophils isolated from CGD mice deficient in gp91 phox (13) was confirmed by monitoring the superoxide dimutase inhibitable reduction of ferricytochrome c (10). Mice were fed rodent diet 5001 (Harlan-Teklad, Madison, Wis.). Between ages 9 and 11 weeks, the mice were injected with one ml of 4% thioglycollate to recruit leukocytes into the peritoneum. The leukocytes were activated 20 hours (h) later by intraperitoneal injection of zymosan (250 mg/kg). Control animals were injected with one ml of buffer A (138 mM NaCl, 3 mM KCl, 0.1 M sodium phosphate, pH 7.4). Prior to and every 2 h during urine collection, the animals were injected intraperitoneally with 2 ml of buffer A.

Urine Collection.

Animals were placed in stainless steel metabolic cages designed for urine collection (21). All subsequent procedures were performed under subdued light. Urine was collected in amber-colored vials containing 40 $\mu$l of 500 $\mu$M diethylenetriaminepentaacetic acid (DTPA, a metal chelator)

and 4 μl of 5% phenol (an antioxidant and bactericidal agent). Collected urine was adjusted to a final concentration of 100 μM DTPA and 0.1% phenol and stored at −80° C. until analysis. Creatinine levels of urine were measured using Sigma Diagnostic Kit 555-A.

Isolation of Amino acid from Urine.

Urine was centrifuged at 10,000×g for 5 min. An aliquot of the urine supernatant (50 μL for mouse and 100 μl for human samples) was supplemented with 0.1% trifluoroacetic acid (TFA; v/v; final volume 200 μl) and $^{13}C$ internal standards. Amino acids were isolated by solid-phase extraction on a C-18 column (3 ml; Supelclean SPE; Supelco, Bellefonte, Pa.) conditioned with 4 ml of methanol and 6 ml of 0.1% TFA. The column was loaded with urine in 0.1% TFA and washed with 2 ml of 0.1% TFA using a vacuum manifold system. Amino acids were eluted with 2 ml of 50% methanol and concentrated to dryness under vacuum for derivatization. Recovery of authentic o,o'-dityrosine subjected to this procedure was>90%.

Leukocyte Harvesting.

Animals were killed by decapitation after metophane-induced anesthesia. After the abdominal wall was washed with 95% ethanol, leukocytes were harvested from the peritoneum using a siliconized glass pipette. The peritoneum was lavaged 3 times with 4 ml of ice-cold Hanks' Balanced Salt Solution (HBSS) containing 100 μM DTPA. Cells were suspended in ice-cold HBSS, collected by low speed centrifugation, and stored at −80° C. until analysis.

Isolation of Amino Acids from Leukocytes.

All procedures were carried out at 4° C. Peritoneal cells were dialyzed against antioxidant buffer (100 μM DTPA, 100 μM butylated hydroxytoluene, 10 mM 3-aminotriazole, 10 mM sodium phosphate, pH 7) and 0.1 mM DTPA (pH 7) and delipidated 3 times with water/methanol/water-washed ether (1:3:7; v/v/v). Residual solvent was removed under vacuum, $^{13}C$ labeled internal standards were added, and protein was hydrolyzed in one ml of 6 N HCl containing 1% phenol at 110° C. for 24 h under argon. Amino acids were isolated from the acid hydrolysate by solid-phase extraction as described above.

Mass Spectrometric Analysis.

Amino acids were converted to their n-propyl esters, heptafluorobutyryl derivatives and quantified by isotope dilution gas chromatography/mass spectrometry (GC/MS) with selected ion monitoring (20,21). Mass spectrometric analysis was performed in the negative ion electron capture mode with methane as the reagent gas, using a Finnigan SSQ with extended mass range equipped with a 12 m DB-1 capillary column (0.2 mm ID, 0.33 μm film thickness; J&W Scientific, Folson, Calif.). The ions monitored were: L-tyrosine, m/z 417 and 595; L-[$^{13}C_6$]tyrosine, m/z 423 and 601; o,o'-dityrosine, m/z 1030 and 1208; o,o'-[$^{13}C_{12}$] dityrosine, m/z 1042 and 1220. Under these conditions, authentic compounds and isotopically labeled standards were baseline separated and exhibited retention times identical to those of analytes.

Metabolic fate of radiolabeled dityrosine.

o,o'-[$^{14}C$]Dityrosine ($2\times10^5$ cpm) was injected into the animals intravenously. Plasma was centrifuged (400×g for 20 min at 4° C.) from blood collected by retro-orbital bleeding. Tissue samples were collected from animals killed by cervical dislocation, weighed and then homogenized in deionized water. Radioactivity in tissue homogenates, plasma, and urine was determined by liquid scintillation spectroscopy (Beckman LS 3801) with correction for quenching. [$^{14}C$]Dityrosine was prepared from L-[$^{14}C$] tyrosine (American Radiolabeled Chemicals Co.; St. Louis, Mo.) and o,o'-[$^{13}C_{12}$]dityrosine was prepared from L-[$^{13}C_6$] tyrosine (Cambridge Isotope Inc.; Andover, Mass.) using horseradish peroxidase (Boehringer Mannheim Biochemicals; Indianapolis, Ind.) and $H_2O_2$ (Fisher Scientific Co.; Pittsburgh, Pa.) and isolated by reverse-phase HPLC; (27). o,o'-[$^{14}C$]Dityrosine and radiolabeled material in urine were analyzed by HPLC (27) using a reverse-phase column (ODS ultrasphere, 250 mm×4.6 mm, particle size 5 μm.; Beckman,) and a flow rate of 1 ml/min. The column was equilibrated with 100% solvent A (1% acetic acid in water). Compounds were eluted with a discontinuous gradient of solvent B (1% acetic acid in methanol). The gradient was 0%–10% solvent B over 10 min, 10% solvent B for 4 min, 10%–100% solvent B over 5 min and 100% solvent B for 10 min. Prior to HPLC analysis, urinary amino acids were isolated by solid-phase extraction as outlined above. Recovery of radiolabeled material from urine subjected to this procedure was>90%. Radioactivity in each HPLC fraction was quantified by liquid scintillation spectroscopy.

Results

To determine whether white blood cells oxidatively damage proteins in vivo, isotope dilution GC/MS was used to quantify levels of o,o'-dityrosine in mouse peritoneal phagocytes. To recruit neutrophils into the peritoneum, the animals were injected with thioglycollate, a chemical irritant. Twenty hours after this first injection, the animals were given an intraperitoneal injection of zymosan, which stimulates phagocytes to produce $H_2O_2$ and secrete myeloperoxidase into the phagolysosome (6). Thioglycollate-injected mice typically yielded $20–40\times10^6$ peritoneal cells. Neutrophils, mononuclear cells, and eosinophils represented 67±4%, 30±4%, and<1% of the harvested phagocytes (n=6 animals).

Acute inflammation increases o,o'-dityrosine levels in urine.

Figure 1A:
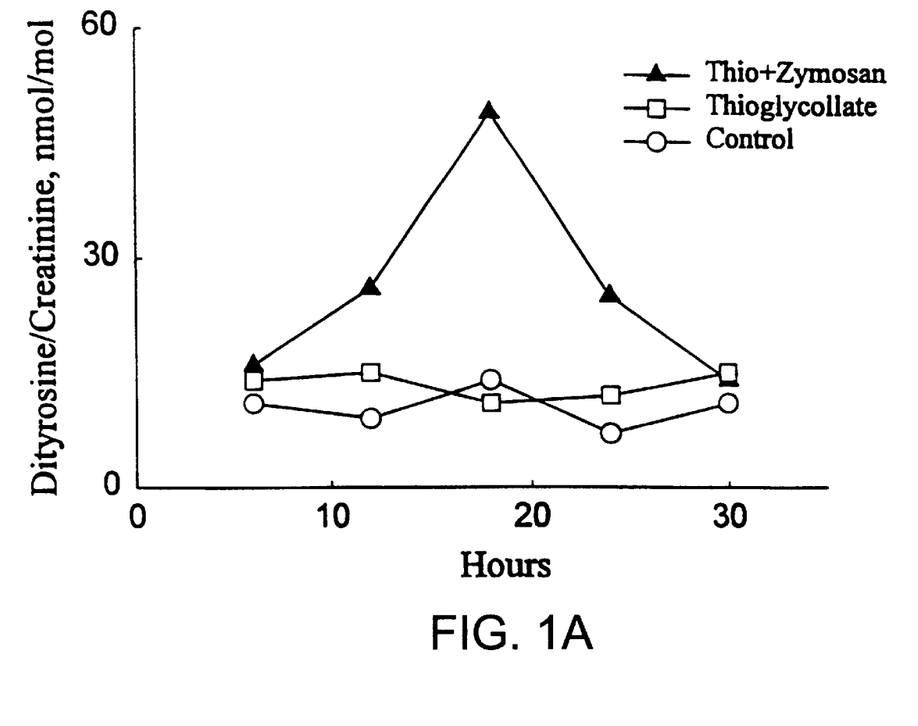
Figure 1B:
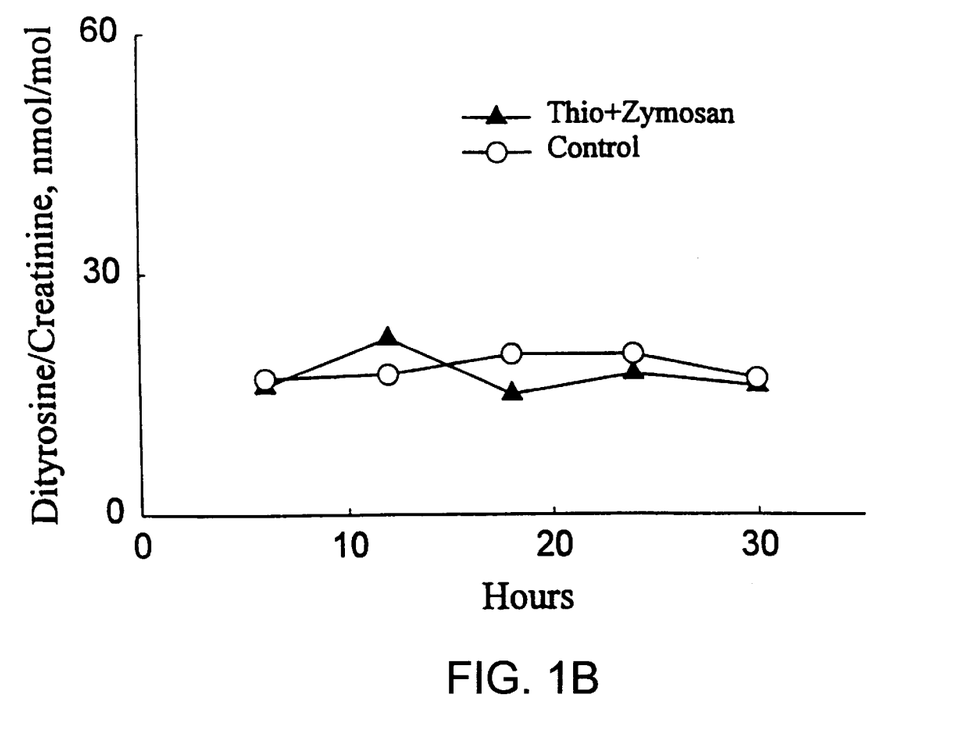

To determine whether animals that develop acute inflammation increase their excretion of o,o'-dityrosine, levels of the oxidized amino acid in urine were measured by negative ion electron capture GC/MS with selected ion monitoring. To correct for individual differences in glomerular filtration, levels of o,o'-dityrosine were normalized to levels of urinary creatinine. The concentration of o,o'-dityrosine was 3-fold greater in the urine of mice injected with thioglycollate and zymosan than in control animals or animals injected with thioglycollate alone (FIG. 1). The increase was maximal 12 h after zymosan injection, and it declined to the baseline level over the next 12 h (FIG. 1A). Urinary o,o'-dityrosine failed to increase in CGD mice injected intraperitoneally with thioglycollate and zymosan (FIG. 1B). These results indicate that degradation of oxidatively damaged proteins in phagocytes releases free o,o'-dityrosine that enters the blood and is excreted in urine.

To investigate whether inflammation might alter the rate at which the kidneys excrete either creatinine or the precursor amino acid of o,o'-dityrosine, levels of creatinine and tyrosine in urine were quantified. There were no differences in creatinine among the animals subjected to the different regimens. The ratio of tyrosine to creatinine in the urine was similar in all groups, suggesting that differential amino acid excretion was not responsible for the differences in o,o'-dityrosine levels that were observed in the urine samples. Moreover, the kinetics and magnitude of o,o'-dityrosine output into the urine of wild-type mice injected with thioglycollate and zymosan were similar when o,o'-dityrosine levels were normalized to urine levels of tyrosine. These results indicate that alterations in renal excretion of creatinine or amino acids do not account for the elevated o,o'-dityrosine levels observed in the urine of wild-type mice subjected to acute inflammation.

Acute inflammation elevates o,o'-dityrosine levels in phagocyte proteins.

Figure 2A:
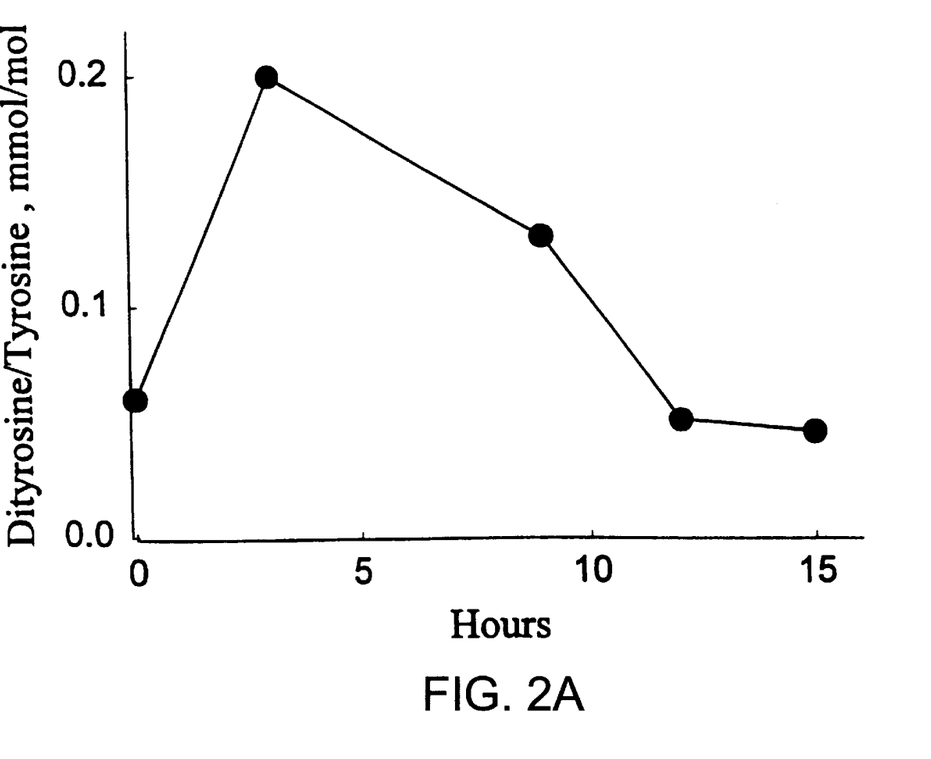

Resident thioglycollate-elicited neutrophils contained ~50 μmol o,o'-dityrosine per mol tyrosine. When neutrophils were exposed to zymosan, however, levels of o,o'-dityrosine in cellular proteins increased 4-fold (FIG. 2A). This increase was transient, peaking at 3 h. Twelve hours after the zymosan injection, the level of protein-bound dityrosine in peritoneal neutrophils was similar to those observed in non-activated neutrophils. These results suggest that activating phagocytes with zymosan transiently increases protein oxidation. The subsequent decline in protein-bound dityrosine may reflect intracellular degradation of oxidized proteins in neutrophils, migration of activated leukocytes out of the peritoneum, or phagocytosis of apoptotic or activated neutrophils by macrophages.

Figure 2B:
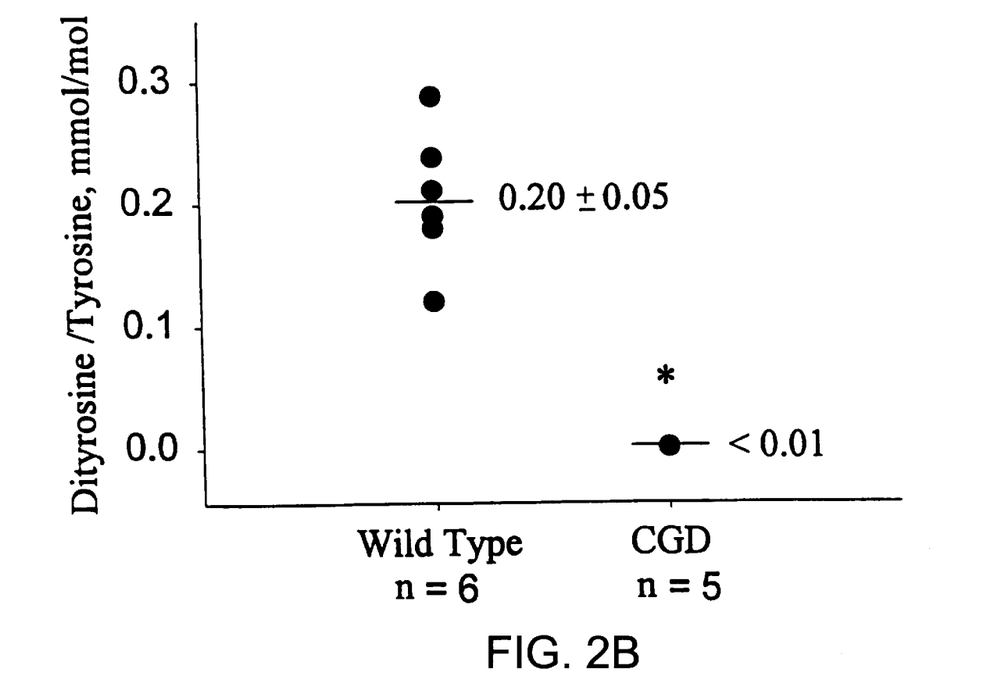

To determine whether reactive oxygen species generated by the NADPH oxidase damage cellular proteins, levels of o,o'-dityrosine were compared after 3 hours of zymosan-stimulation in phagocytes harvested from wild-type and CGD mice (FIG. 2B). The increase in protein-bound dityrosine was completely abrogated in mice deficient in NADPH oxidase ($p<0.0005$). Moreover, o,o'-dityrosine was undetectable in the proteins of these cells, suggesting that oxidants generated by the NADPH oxidase represent the predominant pathway for generation of the tyrosine crosslink in phagocytes. Collectively, these observations indicate that zymosan-stimulated phagocytes oxidatively damage proteins in vivo by a pathway that requires $O_2^{\bullet-}$ and/or $H_2O_2$.

Radiolabeled o,o'-dityrosine is rapidly cleared from the blood and is recovered in near-quantitative yield in urine.

Figure 3A:
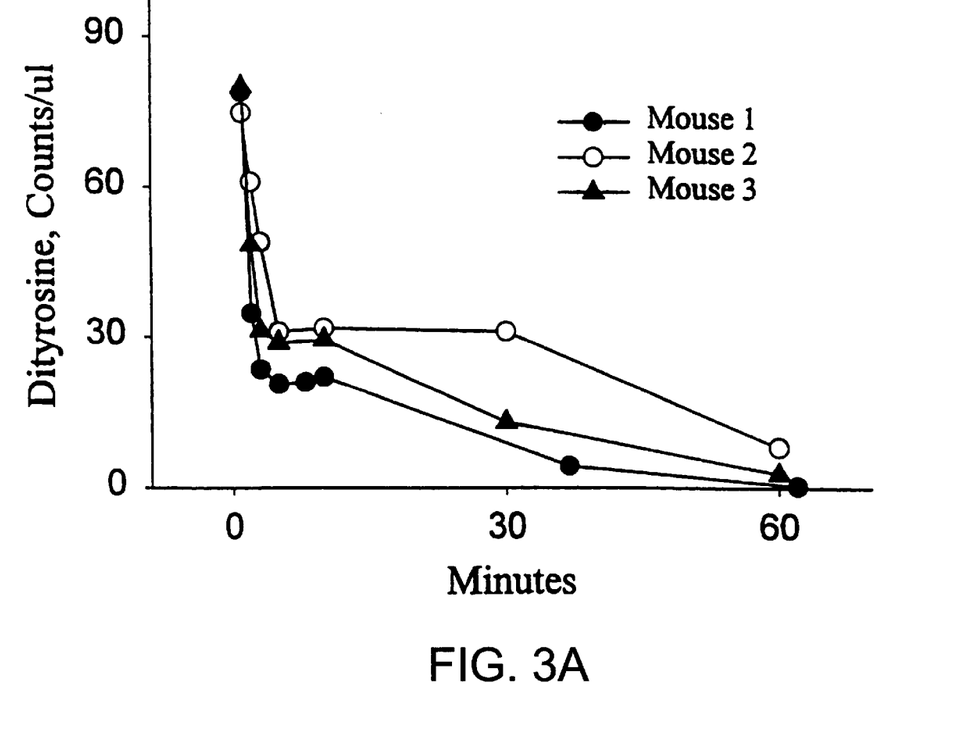
Figure 3B:
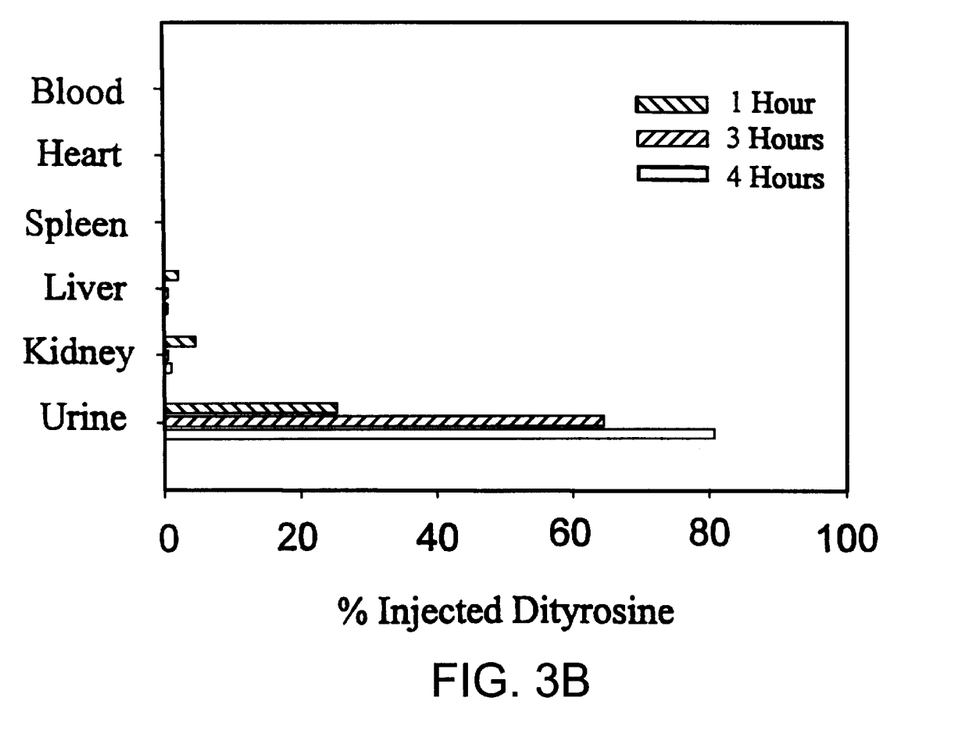
FIG. 3B: Animals were sacrificed at the indicated times after injection of [$^{14}$C]dityrosine. Recovery of radiolabeled material in tissues and urine was quantified by scintillation spectroscopy.

To confirm that free o,o'-dityrosine is excreted in urine and to study the fate of the oxidized amino acid in the body, o,o'-[$^{14}$C]dityrosine was injected intravenously into mice and the amount of radioactivity that subsequently appeared in blood, tissue, and urine samples was measured (FIG. 3). Dityrosine was cleared from the blood with biphasic kinetics (FIG. 3A). It initially disappeared rapidly, with more than 50% of the radiolabeled material lost 5 min after injection. Its subsequent disappearance was slower, with an apparent half-life in the blood of ~30 min. Thirty percent of the radioactivity was recovered in the urine 1 h after intravenous injection of o,o'-[$^{14}$C]dityrosine, 65% was recovered after 3 h, and 81% was recovered after 4 h (FIG. 3B). In striking contrast, radiolabeled material was essentially undetectable in blood, liver, spleen, and heart. Small amounts (<5%) were present in kidney, perhaps due to urine in the renal collecting system. These results indicate that free o,o'-dityrosine is rapidly cleared from blood and quantitatively recovered in urine, strongly suggesting that the oxidized amino acid is filtered from the blood by the kidneys and excreted in urine. They also suggest that cells do not take up o,o'-dityrosine from blood and incorporate it into proteins to a significant degree.

Figure 4:
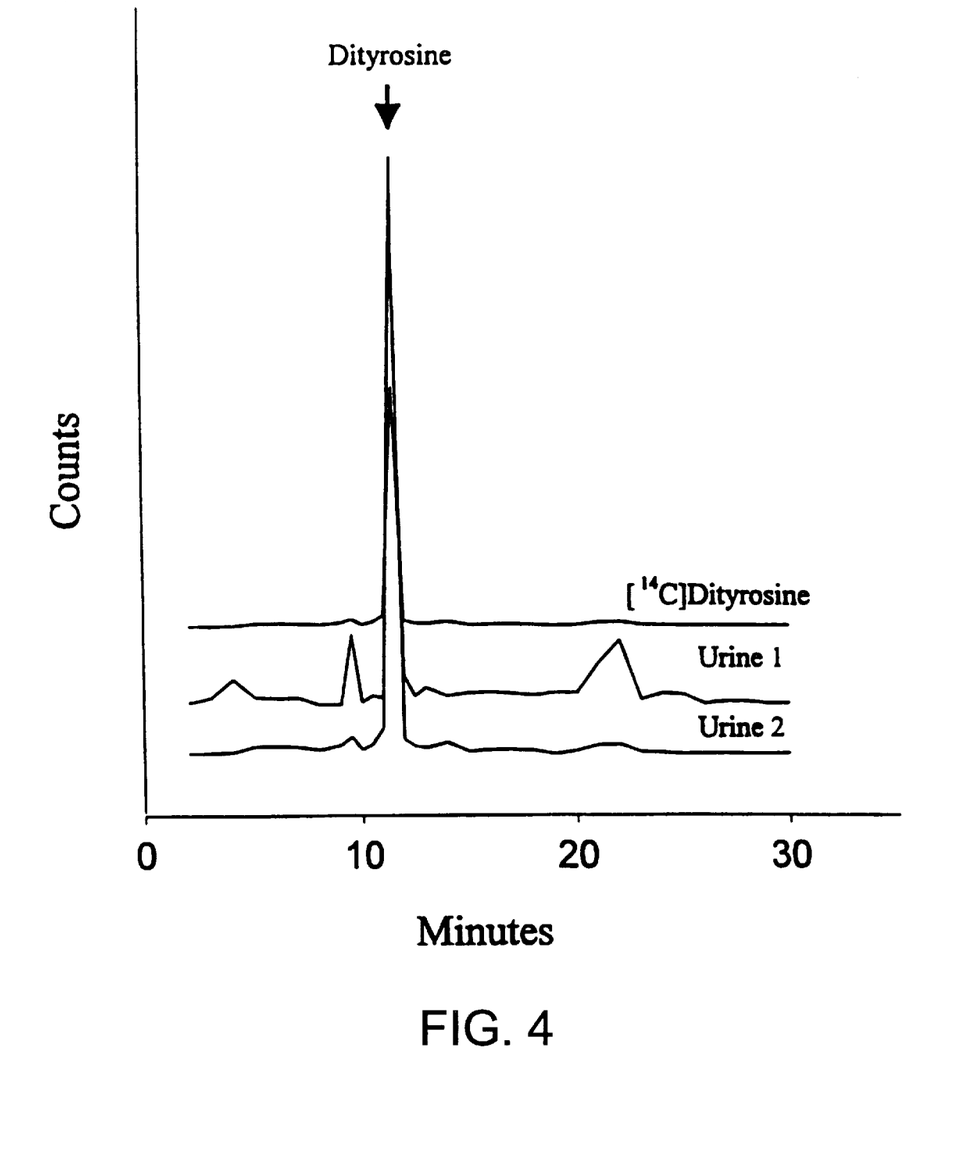
FIG. 4 is graphical representation of HPLC in which Counts are plotted against time in minutes for urinalysis.

To determine whether any of the o,o'-dityrosine that was injected intravenously was metabolized prior to excretion, the radiolabeled material that appeared in urine was subjected to reverse-phase HPLC analysis (FIG. 4). Previous studies have shown that this chromatography system readily separates a wide range of tyrosine oxidation products (27). More than 80% of the radioactivity in the present samples co-migrated with authentic o,o'-[$^{14}$C]dityrosine. These results indicate that most of the radiolabeled material that was injected into the animals and recovered from urine was free o,o'-[$^{14}$C]dityrosine under the analytical conditions used herein. The remaining radiolabeled material likely represents metabolites derived from o,o'-[$^{14}$C]dityrosine.

The urine of septic humans is enriched in o,o'-ditvrosine.

Figure 5A:
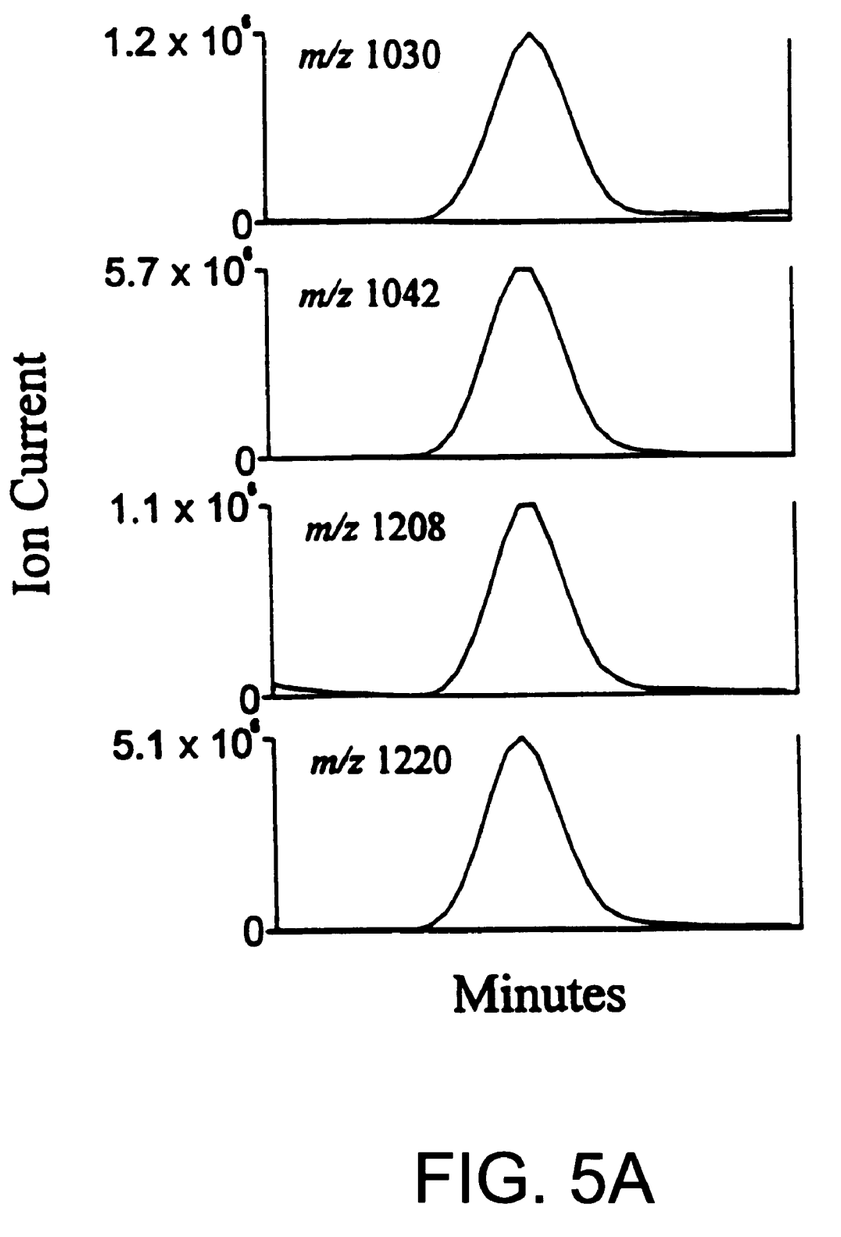
Figure 5B:
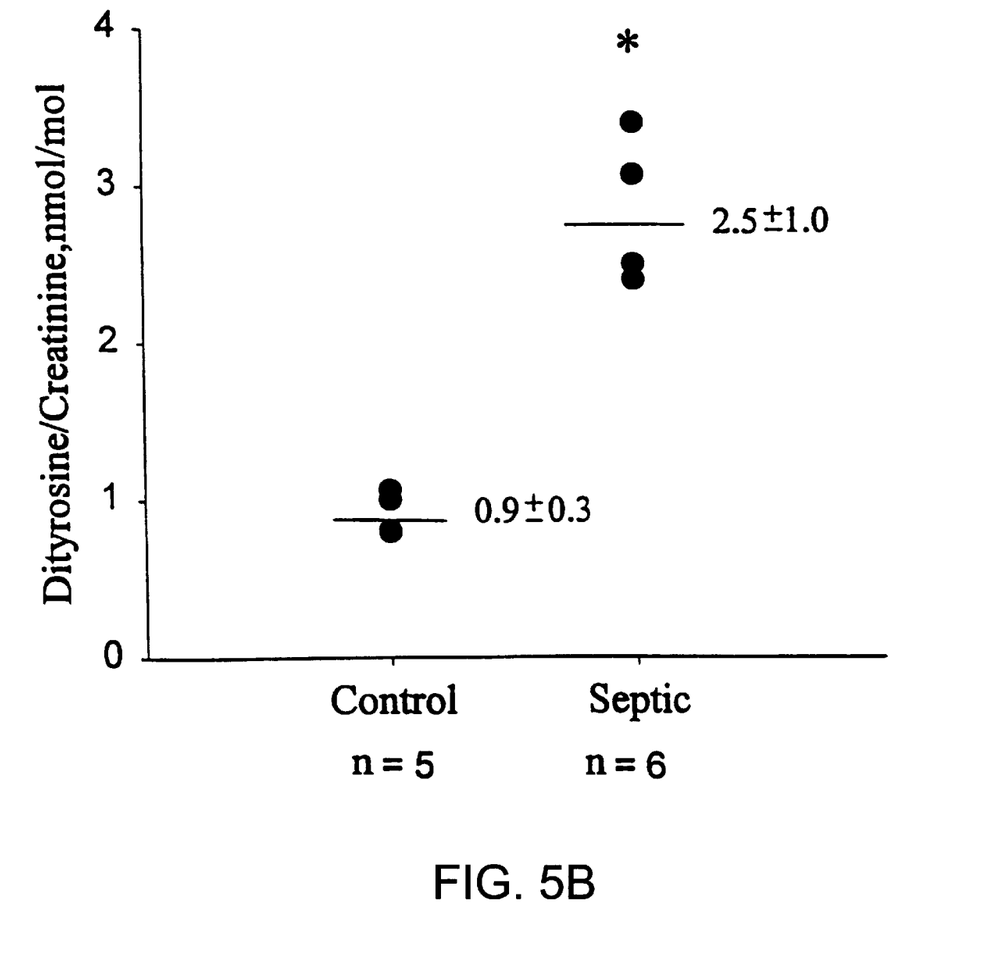
FIG. 5B: Isotope dilution GC/MS quantification of o,o'-dityrosine in the urine of healthy and septic humans. *$p<0.005$ compared with control, Student's t test.

To confirm the utility of o,o'-dityrosine as a clinical marker of oxidative stress, isotope dilution GC/MS was used to quantify the oxidized amino acid in human urine (FIG. 5). Selected ion monitoring demonstrated that the negative ions derived from derivatized o,o'-dityrosine co-eluted with ions derived from authentic $^{13}$C-labeled internal standards in these samples (FIG. 5A). Urine from acutely ill patients with sepsis (fever, elevated white blood cell count and a known source of infection) had a three-fold increase (FIG. 5B, $p<0.005$) in the concentration of o,o'-dityrosine compared with urine from young, healthy subjects (20 to 40 years old). These results indicate that healthy humans excrete o,o'-dityrosine in urine and that levels of the oxidized amino acid are markedly elevated in septic patients.

In the above examples, isotope dilution GC/MS was used to simultaneously quantify levels of o,o'-dityrosine in both inflammatory cells and urine of wild-type and CGD mice. The use of CGD mice allowed assessment of the role of phagocyte NADPH oxidase in promoting protein oxidation in vivo. o,o'-Dityrosine levels were monitored for four reasons.

First, previous in vitro studies have shown that activated phagocytes produce oxidants that generate o,o'-dityrosine by pathways that involve tyrosyl radical generated by myeloperoxidase, reactive nitrogen species, or hydroxyl radical (16–19,28).

Second, elevated levels of protein-bound dityrosine—a specific marker of oxidation—have been detected in various pathological states, suggesting that tyrosyl radical may be one agent that promotes oxidative stress in vivo.

Third, in vitro studies indicate that o,o'-dityrosine serves as a marker for the proteolysis of oxidized proteins in red blood cells exposed to $H_2O_2$ (24).

Finally, it was believed that this cross-linked amino acid was likely to be excreted from the body in urine rather than used to synthesize new proteins.

The above results indicate that stimulating phagocytes with zymosan in vivo markedly increases their content of protein-bound dityrosine. This increase failed to occur in CGD mice, implicating phagocyte activation and the NADPH oxidase in protein oxidation (1,14,16–18,28,29). The level of phagocyte o,o'-dityrosine peaked 3 h after the cells were activated; it then rapidly returned to that observed in quiescent phagocytes. Importantly, the concentration of o,o'-dityrosine in urine also increased in this mouse model of acute inflammation. Again, this increase was inhibited in CGD mice. Urinary o,o'-dityrosine levels peaked 12 h after stimulation of the cells with zymosan, following the transient increase in phagocyte o,o'-dityrosine levels. Collectively, these observations indicate that activated phagocytes oxidatively modify proteins during inflammation by a pathway dependent upon NADPH oxidase, implicating $O_2^{\bullet-}$ and/or $H_2O_2$ in the reaction. The kinetics of its appearance in cells and then urine strongly confirm that oxidatively modified proteins undergo proteolysis and that the liberated o,o'-dityrosine is excreted in urine.

o,o'-Dityrosine was detected in the urine of healthy humans, but the concentration was three times as high in the urine of patients suffering from systemic bacterial infections. Bacteria are known to activate phagocytes, whose NADPH oxidase plays a key role in host defenses against invading pathogens (1,6,14). This indicates that oxidants generated by phagocytes are one physiologically relevant pathway for protein oxidation in humans. Therefore, assaying o,o'-dityrosine is a useful approach to monitoring oxidative stress in vivo.

It is noteworthy that o,o'-dityrosine is present in the tissues and urine of healthy young humans and control animals. This indicates that pathways not involving phagocyte NADPH oxidase also can generate this oxidized amino acid. Heme proteins and hydroxyl radical-like species generated by mitochondria represent other mechanisms for o,o'-dityrosine formation in vivo (21,22). The use of mice with genetically engineered alterations in these pathways provides a powerful test of this mechanism.

An important point regarding the use of o,o'-dityrosine to monitor oxidative stress in vivo is the fate of the cross-linked amino acid in the body. For example, o,o'-dityrosine might be re-incorporated into proteins or metabolized to other compounds, invalidating the relationship between its concentration in urine and protein oxidation. This issue was addressed by injecting purified radiolabeled o,o'-dityrosine intravenously into mice and monitoring the disappearance of the oxidized amino acid from blood. More than half of the radiolabel disappeared from the blood in 5 min, indicating that o,o'-dityrosine is taken up by tissues or excreted into the urine by the kidney. Between 3 h and 4 h later, the radioactive material was recovered almost quantitatively in the urine. Analysis by reverse-phase HPLC with a gradient that separates a wide variety of tyrosine oxidation products (27) indicated that most of the radioactivity comigrated with authentic o,o'-dityrosine. These results indicate that o,o'-dityrosine released from proteins is excreted in urine in near-quantitative yield and that the oxidized amino acid in blood is relatively resistant to metabolism into other compounds.

These in vivo results suggest the following model. Activated phagocytes use oxidants produced by the NADPH oxidase to generate tyrosyl radical or other reactive species that form o,o'-dityrosine cross-links in proteins. The oxidized proteins then are selectively targeted for proteolytic degradation (4,24–26). Alternatively, macrophages may phagocytose and digest neutrophils that have been activated and are undergoing apoptosis (30,31). The resulting free oxidized amino acids are released from cells, enter the blood, are filtered out of the blood by the kidneys, and excreted in near-quantitative yield in the urine. This model is consistent with the above results whereby quantifying o,o'-dityrosine and other oxidized amino acids in urine may provide a noninvasive method for measuring protein oxidative stress in vivo. Such an assay is invaluable for assessing the role of oxidative stress in aging and the pathogenesis of human disease.

REFERENCES

1. Klebanoff, S. J. (1980) *Ann. Intern. Med.* 93, 480–489.
2. Baynes, J. W. (1991) *Diabetes*, 405–412.
3. Berliner, J. A. & Heinecke, J. W. (1996) *Free Radical Biology & Medicine* 20, 707–727.
4. Stadtman, E. R. (1992) *Science* 257, 1220–1224.
5. Ames, B. N., Shigenaga, M. K. & Hagen, T. M. (1993) *Proc. Natl. Acad. Sci. U.S.A.* 90, 7915–7922.
6. Klebanoff, S. J. & Clark, R. A. (1978) The Neutrophil. (North Holland Biochemical Press, Amsterdam), pp. 447–451.
7. Hurst, J. K. & Barrette, W. C., Jr. (1989) *CRC Crit. Rev. Biochem. Mol. Biol.*, Vol. 24, pp. 271–328.
8. Segal, A. W. & Abo, A. (1993) *Trends Biochem. Sci.* 18, 43–47.
9. Babior, B. M. (1999) *Blood* 93, 1464–76.
10. Babior, B. M., Kipnes, R. S., Curnutte, J. T. (1973) *J. Clin. Invest.* 52, 741–744.
11. Nauseef, W. M. (1999) *Proc. Assoc. Am. Physicians* 111, 373–82.
12. Meischl, C., Roos, D. (1998) *Springer Semin. Immunopathol.* 19, 417–34.
13. Pollock, J. D., Williams, D.A., Gifford, M.A., Li, L.L., Du, X.,.Fisherman, J., Orkin, S. H., Doerschuk, C. M., Dinauer, M. C., (1995) *Nat. Genet.* 9, 202–209.
14. Babior, B. M. (1978) *N. Engl. J. Med.* 298, 659–663.
15. Heinecke, J. W. (1997) *Cur. Opinions Lipid.* 8:268–274.
16. Heinecke, J. W., Li, W., Daehnke, H. L., Goldstein, J. A. (1993) *J. Biol. Chem.* 268, 4069–4077.
17. Heinecke, J. W., Li, W., Francis, G. A., Goldstein, J. A. (1993) *J. Clin. Invest.* 91, 2866–2872.
18. Van dervliet, A., EiBerich, J. P., Halliwell, B., Cross, C. E. (1997) *J. Biol. Chem.* 272, 7617–7625.
19. Huggins, T. G., Wells-Knecht, M. C., Detorie, N. A., Baynes, J. W., Thorpe, S. R. (1993) *J. Biol. Chem.* 268, 12341–12347.
20. Leeuwenburgh, C., Rasmussen, J. E., Hsu, F. F., Mueller, D. M., Pennathur, S., Heinecke, J. W. (1997) *J. Biol.Chem.* 272, 3520–3526.
21. Leeuwenburgh, C., Hansen, P. A., Holloszy, J. O., Heinecke, J. W. (1999) *Am. J. Physiol.* 45, R128–R135.
22. Leeuwenburgh, C., Hansen, P. A., Holloszy, J. O., Heinecke, J. W., (1999) *Free Rad. Biol. Med.* 27, 186–192.
23. Hensley, K., Maidt. M. L., Yu, Z. Q., Sang, H., Markesbery, W. R., Floyd, R. A., (1998) *J. Neurosci.* 18, 8126–8132.
24. Giulivi, C., and Davies, K. J. A. (1993) *J.Biol. Chem.* 268, No 12, 8752–8759.
25. Dean, R. T. F., S. Stocker, R. Davies, M. J. (1997) *Biochem. J May* 15;324 (Pt-1): 1–18
26. Davies, K. J. A. (1987) *J. Biol. Chem.*, 9895–9901.
27. Jacob, J. S., Cistola, D. P., Hsu, F. F., Muzaffar, S., Mueller, D. M., Hazen, S. L., Heinecke, J. W. (1995) *J. Biol. Chem.* 271, 19950–19956.
28. McCormick, M. L., Gaut, J. P., Lin, T. S., Britigan, B. E., Buettner, G. R.,Heinecke, J. W. (1998) *J. Biol. Chem.* 273, 32030–32037.
29. Heinecke J. W. (1999) *FASEB J.* 13:1113–1120.
30. Homburg, C. H., Roos, D. (1996) *Curr. Opin. Hematol.*1, 94–99.
31. Savill, J. (1997) *J. Leukoc. Biol.* 61, 375–80.

What is claimed:

1. A non-invasive method for the determination of oxidative stress in a patient comprising quantifying the level of o,o'-dityrosine in a sample of said patient's urine and comparing with the corresponding level of said compound in a normal or control sample, whereby a substantially elevated level of said o,o'-dityrosine is indicative of oxidative stress in said patient.

2. The method of claim 1 in which the level of o,o'-dityrosine is quantified by gas chromatography together with mass spectrometry.

* * * * *